US009170371B2

(12) United States Patent
Santori et al.

(10) Patent No.: US 9,170,371 B2
(45) Date of Patent: Oct. 27, 2015

(54) MICRO-RING OPTICAL RESONATORS (75) Inventors: Charles M. Santori, Palo Alto, CA (US); Marco Fiorentino, Mountain View, CA (US); Zhen Peng, Foster City, CA (US); David A. Fattal, Mountain View, CA (US); Andrei Faraon, Menlo Park, CA (US); Raymond G. Beausoleil, Redmond, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 757 days.

(21) Appl. No.: 13/454,462

(22) Filed: Apr. 24, 2012

(65) Prior Publication Data
US 2013/0279849 A1 Oct. 24, 2013

(51) Int. Cl.
*G02B 6/26* (2006.01)
*G02B 6/12* (2006.01)
*G02B 6/34* (2006.01)
*G02B 6/42* (2006.01)

(52) U.S. Cl.
CPC .............. *G02B 6/12016* (2013.01); *G02B 6/34* (2013.01); *G02B 6/4215* (2013.01); *G02B 6/4287* (2013.01)

(58) Field of Classification Search
None
See application file for complete search history.

(56) References Cited

U.S. PATENT DOCUMENTS

| | | | | |
|---|---|---|---|---|
| 5,274,720 A * | 12/1993 | Yamamoto | | 385/129 |
| 6,563,966 B1 * | 5/2003 | Tang | | 385/10 |
| 6,959,028 B2 * | 10/2005 | Jones | | 372/94 |
| 7,324,199 B2 | 1/2008 | Ja et al. | | |
| 7,361,501 B2 | 4/2008 | Koo et al. | | |
| 7,529,435 B2 * | 5/2009 | West et al. | | 385/14 |
| 7,796,262 B1 * | 9/2010 | Wang et al. | | 356/436 |
| 8,059,922 B2 | 11/2011 | Fattal et al. | | |
| 2007/0223859 A1 | 9/2007 | Kornilovich et al. | | |
| 2009/0028487 A1 | 1/2009 | Fattal et al. | | |
| 2010/0110443 A1 | 5/2010 | Cheben et al. | | |
| 2011/0273709 A1 | 11/2011 | Sweeney | | |
| 2013/0085398 A1 * | 4/2013 | Roukes | | 600/478 |
| 2013/0119270 A1 * | 5/2013 | Suh et al. | | 250/458.1 |
| 2013/0259747 A1 * | 10/2013 | Lee et al. | | 422/69 |

FOREIGN PATENT DOCUMENTS

WO WO2011140544 11/2011

OTHER PUBLICATIONS

Soltani, et al., "Large-scale Array of Small High-Q Microdisk Resonators for on chip Spectral Analysis," LEOS Annual Meeting Conference Proceedings, Aug. 17-20, 2009, pp. 703-704.

Xia et al., "Large-scale Array of Miniaturized Microdonut Resonators for High Resolution On-chip Spectroscopy," OSA/CLEO, May 16-21, 2010, CTuL3, 2 pages.

Xia et al., "High resolution on-chip spectroscopy based on miniaturized microdonut resonators," Optics Express vol. 19, No. 13, Published Jun. 10, 2011, pp. 12356-12364.

(Continued)

*Primary Examiner* — Tina Wong
(74) *Attorney, Agent, or Firm* — Brooks, Cameron & Huebsch, PLLC (57) ABSTRACT

Apparatuses, systems, and methods for micro-ring optical resonators are provided. An example of a micro-ring optical resonator apparatus includes an array of input waveguides with each input waveguide optically coupled to an array of micro-rings, an output waveguide operatively associated with each of the micro-rings, and a scattering object operatively associated with each of the micro-rings, wherein the scattering object is connected to the output waveguide.

20 Claims, 7 Drawing Sheets

(56) References Cited

OTHER PUBLICATIONS

Chang et al., "On the estimation of target spectrum for filter array based spectrometers," Optics Express vol. 16, No. 2, Published Jan. 14, 2008, pp. 1056-1061.

Ismail et al., "Raman spectroscopy with an integrated arrayed-waveguide grating," Optics Letters vol. 36, No. 23, Dec. 1, 2011, pp. 4629-4631.

Brouckaert, et al., "Silicon-on-Insulator Microspectrometer," Proceedings Symposium IEEE/LEOS Benelux Chapter, Nov. 27-28, 2008, pp. 7-10.

\* cited by examiner

MICRO-RING OPTICAL RESONATORS

BACKGROUND

Transmission of light through waveguides has been used for many types of applications. Light signals offer potential advantages over electronic signals. Light can be input from a variety of sources.

Optical spectroscopy, for instance, is useful in a variety of fields, such as physics, astronomy, chemistry, biology, and medicine, among others. Raman spectroscopy, for instance, can use a laser to produce light that interacts with a sample to produce frequency-shifted light, thereby providing an optical fingerprint of the sample's molecular structure. Using such a system, for instance, requires an ability to collect and identify the optical fingerprint.

DETAILED DESCRIPTION

Examples of the present disclosure include apparatuses, systems, and methods for micro-ring optical resonators. An example of a micro-ring optical resonator apparatus includes an array of input waveguides with each input waveguide optically coupled to an array of micro-rings, an output waveguide operatively associated with each of the micro-rings, and a scattering object operatively associated with each of the micro-rings, wherein the scattering object is connected to the output waveguide.

Apparatuses, systems, and methods that include micro-ring optical resonators, as described herein, have applicability in many fields in which spectroscopy is utilized, such as in physics, astronomy, chemistry, biology, and medicine, among others. An example is Raman spectroscopy (e.g., surface-enhanced Raman spectroscopy (SERS)), in which a laser interacts with a sample to produce frequency-shifted scattered light, thereby providing a molecular fingerprint of the sample's molecular structure. A compact, low-cost spectrometer that can be used in the field would be beneficial for Raman spectroscopy. However, a spectrometer having a resolution below 100 gigahertz (GHz) often involves a large grating-based monochromator. The apparatuses and systems described herein are designed to reduce the size and/or weight of spectrometers (e.g., compared to the large grating-based monochromators), while also providing high throughput and resolution. Another application described herein is hyper-spectral imaging using an apparatus (e.g., a chip-scale apparatus) that allows for spectroscopic imaging in many different frequency (e.g., wavelength) bands in parallel.

Figure 1:
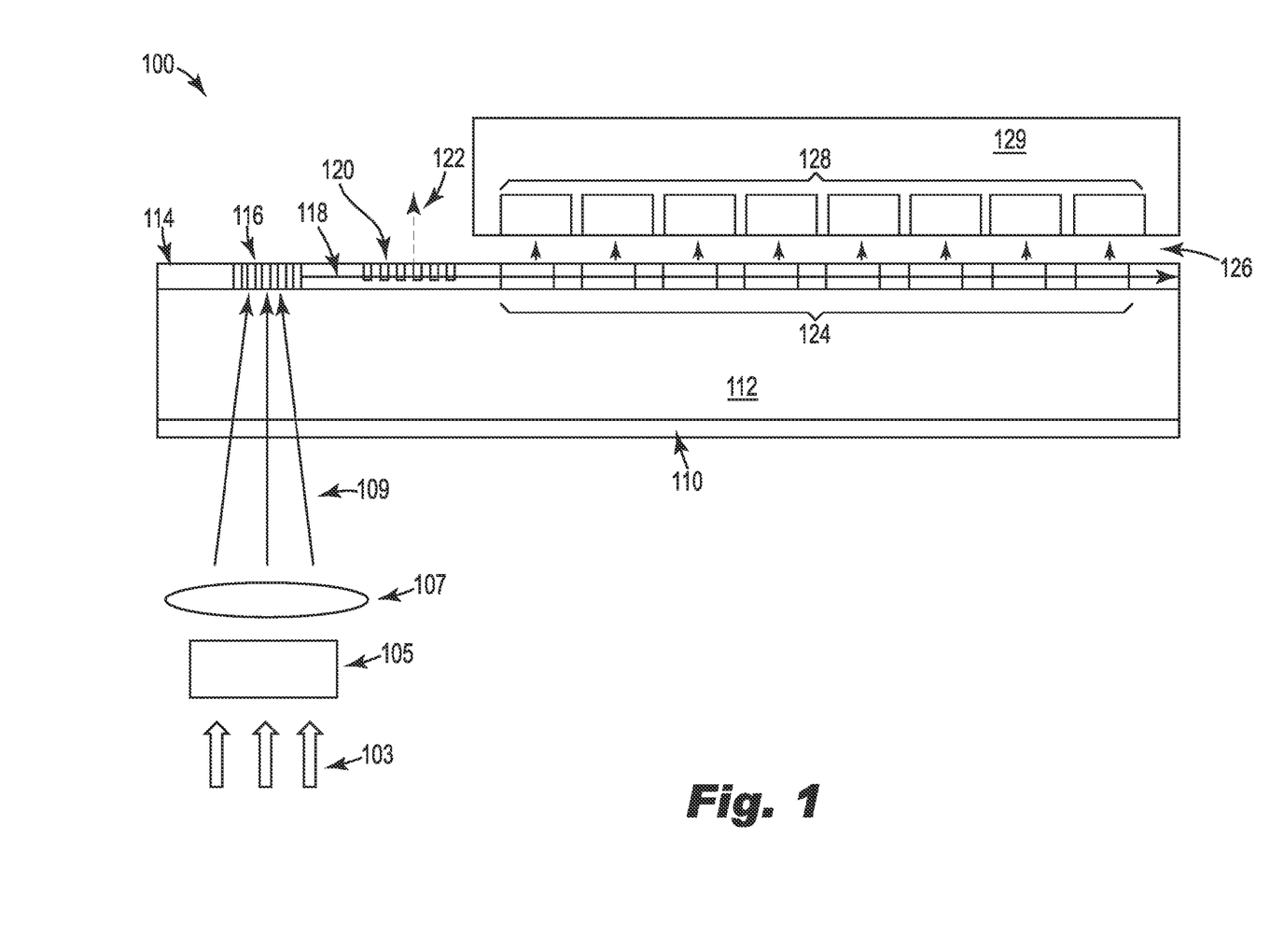
FIG. 1 illustrates an example of an input waveguide coupled to micro-ring optical resonators in association with a measurement device according to the present disclosure.

FIG. 1 illustrates an example of an input waveguide coupled to micro-ring optical resonators in association with a measurement device according to the present disclosure. In the following Detailed Description and Figures, some features are grouped together in a single example (e.g., embodiment) for the purpose of streamlining the disclosure. This manner of presentation is not to be interpreted as reflecting an intention that the disclosed embodiments require more features (e.g., elements and/or limitations) than are expressly recited in the claims of the present disclosure. Rather, as the following claims reflect, inventive subject matter may require less than all features of a single disclosed example. Hence, the following claims are hereby incorporated into the Detailed Description, with each claim standing on its own merit as a separate embodiment.

Micro-ring optical resonators as described in the present disclosure can be utilized with an input waveguide coupled to a plurality of such micro-ring optical resonators. For brevity, such micro-ring optical resonators can be referred to herein as a "micro-ring" in the singular and "micro-rings" in the plural. As described herein, in some examples, differently configured micro-rings that resonate to different frequencies of light can serve as drop filters to transmit these specific frequencies (e.g., as light, energy, and/or signals) to detectors (e.g., to a measurement device designed to collect such light, energy, and/or signals).

As illustrated in FIG. 1, the example of the input waveguide coupled to the micro-rings 100 includes input light 103, which can include a range of frequencies and/or wavelengths originating from a variety of sources, directed toward the input waveguide coupled to the micro-rings 100. As previously indicated, the example shown in FIG. 1 includes optional features. A coarse frequency sorting element 105 can, in some examples, be included for separation of input light into a plurality of different input ranges of optical frequencies (e.g., using a prism, an arrayed wavelength grating (AWG), an echelle grating, among others) and/or a focusing lens 107 to accurately direct and/or concentrate (e.g., using a micro-lens) the resultant input light 109 for the input waveguide coupled to the micro-rings 100. The resultant input light 109 (e.g., which may, in some examples, be the same as the original input light 103) can, for example, be collected by an input coupler 116 connected to (e.g., integrated with) an input waveguide 114. The features shown in FIG. 1 are illustrated from a side view perspective, whereas the features in other figures are illustrated from a top view perspective.

In the detailed description of the present disclosure, reference is made to the accompanying drawings that form a part hereof and in which is shown by way of illustration how examples of the disclosure may be practiced. These examples are described in sufficient detail to enable those of ordinary skill in the art to practice the examples of this disclosure and it is to be understood that other examples may be utilized and that process, electrical, and/or structural changes may be made without departing from the scope of the present disclosure. Further, where appropriate, as used herein, "for example" and "by way of example" should be understood as abbreviations for "by way of example and not by way of limitation".

The figures herein follow a numbering convention in which the first digit or digits correspond to the drawing figure number and the remaining digits identify an element or component in the drawing. Similar elements or components between different figures may be identified by the use of similar digits. For example, 111 may reference element "11" in FIG. 1, and a similar element may be referenced as 211 in FIG. 2. Elements shown in the various figures herein may be added, exchanged, and/or eliminated so as to provide a number of additional examples of the present disclosure. In addition, the proportion and the relative scale of the elements provided in the figures are intended to illustrate the examples of the present disclosure and should not be taken in a limiting sense.

The input waveguide 114 illustrated in FIG. 1 can be formed from various materials. For example, a first waveguide, as described herein, can be formed using a first material, and a second input waveguide can be formed using a second material that is different from the first material. The different materials can be selected and/or configured to retain and/or transmit, for example, different frequencies or ranges of frequencies of light. Examples of such materials include silicon nitride and silicon carbide (e.g., on silicon oxide, among others), which allow transmission of light through visible and/or near infrared frequencies.

In some examples, an input waveguide can be supported by a substrate 112 (e.g., formed from a substantially transparent material). In various examples, the substrate 112 can include a number of layers having refractive and/or reflective indices that differ from those of the input waveguide 114. In some examples, the substrate 112 can be interfaced with (e.g., on an opposite surface from a surface supporting the input waveguide 114) a number of layers of dielectric material 110 (e.g., a dielectric stack) serving as a filter for the input light 103, 109. In some examples, the dielectric material can be positioned between the input waveguide 114 and the substrate 112. As such, the opposite surface from the surface supporting the input waveguide 114 can, in some examples, be interfaced with an anti-reflective coating (not shown).

The input coupler 116 integrated with the input waveguide 114 illustrated in FIG. 1, in various examples, can be or can include a grating coupler. Such a grating coupler can have a grating with a predetermined pitch, etch angle, and/or duty cycle for diffraction of incident light 109, for example, such that the incident light 109 becomes light 118 that travels in an intended direction along the input waveguide 114.

In some examples, the input waveguide 114 can be integrated with a grating filter 120. Such a grating filter 120 may be configured (e.g., with a predetermined pitch, etch angle, and/or duty cycle) for diffraction and/or back reflection of a particular frequency or range of frequencies 122 of the light 118 traveling along the input waveguide 114. For example, the particular frequency or range of frequencies 122 may correspond to output from a laser (e.g., utilized in SERS), the output frequencies of which are not of interest in downstream analysis. As such, the particular frequency or range of frequencies 122 can, in some examples, be diffracted and/or scattered out of the input waveguide 114 (e.g., before the light 118 traveling in the intended direction along the input waveguide 114 reaches a first micro-ring).

The light 118 traveling along the input waveguide 114 can interact with a plurality of micro-rings 124. The plurality of micro-rings 124 are illustrated in FIG. 1 from a side view perspective. However, as shown in other figures illustrated from a top view perspective, the plurality of micro-rings 124 is laterally offset from the input waveguide 114 (e.g., some or all of the plurality of micro-rings 124 can be in front of and/or behind the input waveguide 114 shown in FIG. 1).

As described herein, each of the micro-rings in the plurality of micro-rings 124 can be configured to resonate to a particular frequency or range of frequencies present in the light 118 traveling along the input waveguide 114. For example, each of the micro-rings in the plurality of micro-rings 124 can resonate to a different frequency or a different range of frequencies.

The frequency or frequencies at which a particular micro-ring will resonate can depend on a number of factors related to the physical structure of the particular micro-ring. For example, factors such as diameter, circumference, and/or thickness of the micro-ring, a proportion of the diameter contributing to a hole in the middle of the micro-ring, and/or a particular material or compound from which the micro-ring is formed, among other factors, can be selected to determine the frequency or frequencies at which the particular micro-ring will resonate. In some examples, the frequency or frequencies at which a particular micro-ring resonates can be determined experimentally and a number of these factors can be subsequently adjusted to achieve a selected resonant frequency or range of frequencies.

Consequently, each of the micro-rings in the plurality of micro-rings 124 can be configured (e.g., selected), as described herein, to emit light, energy, and/or signals 126 corresponding to the particular frequency or range of frequencies present in the light 118 traveling along the input waveguide 114. Such emitted light, energy, and/or signals 126 can, in various examples, be collected by detectors 128, which can be included in a measurement device 129, designed to collect such light, energy, and/or signals. The individual detectors 128 (e.g., photoactive sensors) of the measurement device 129 (e.g., a charge coupled device (CCD)) can, in various examples, be co-aligned with each of the plurality of micro-rings 124.

Figure 2A:
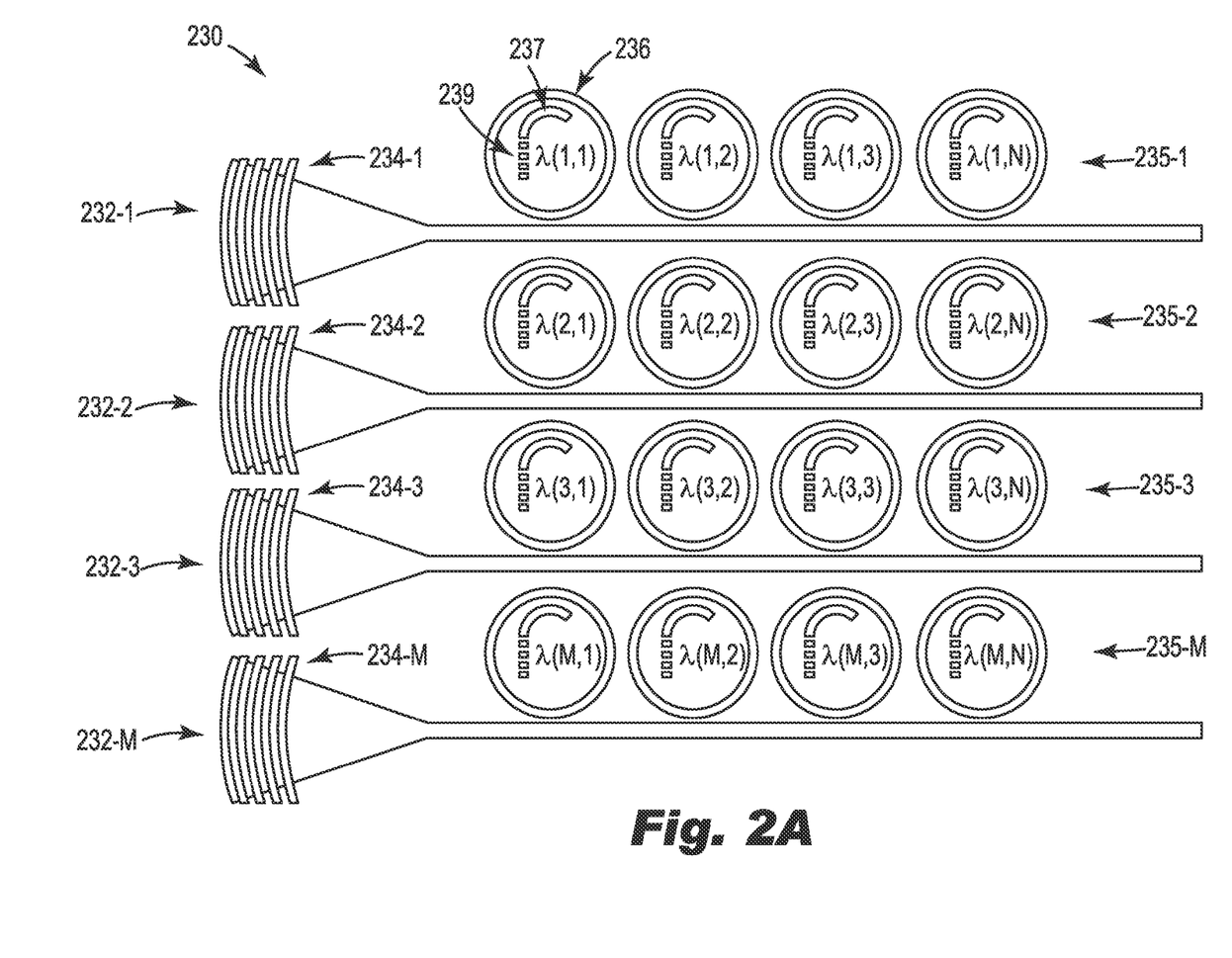
FIGS. 2A-2C illustrate examples of an array of input waveguides coupled to micro-ring optical resonators according to the present disclosure.
Figure 2B:
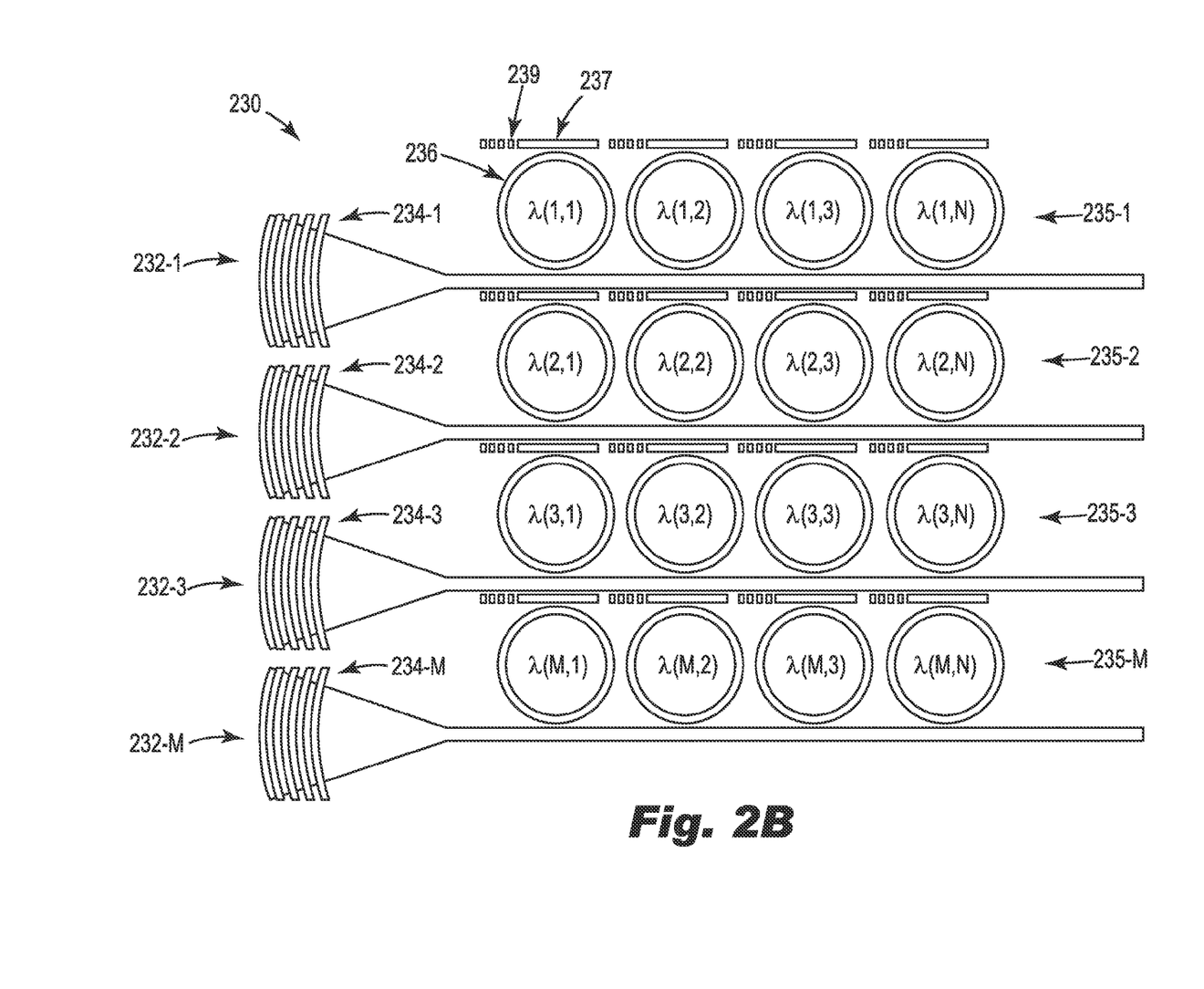
Figure 2C:
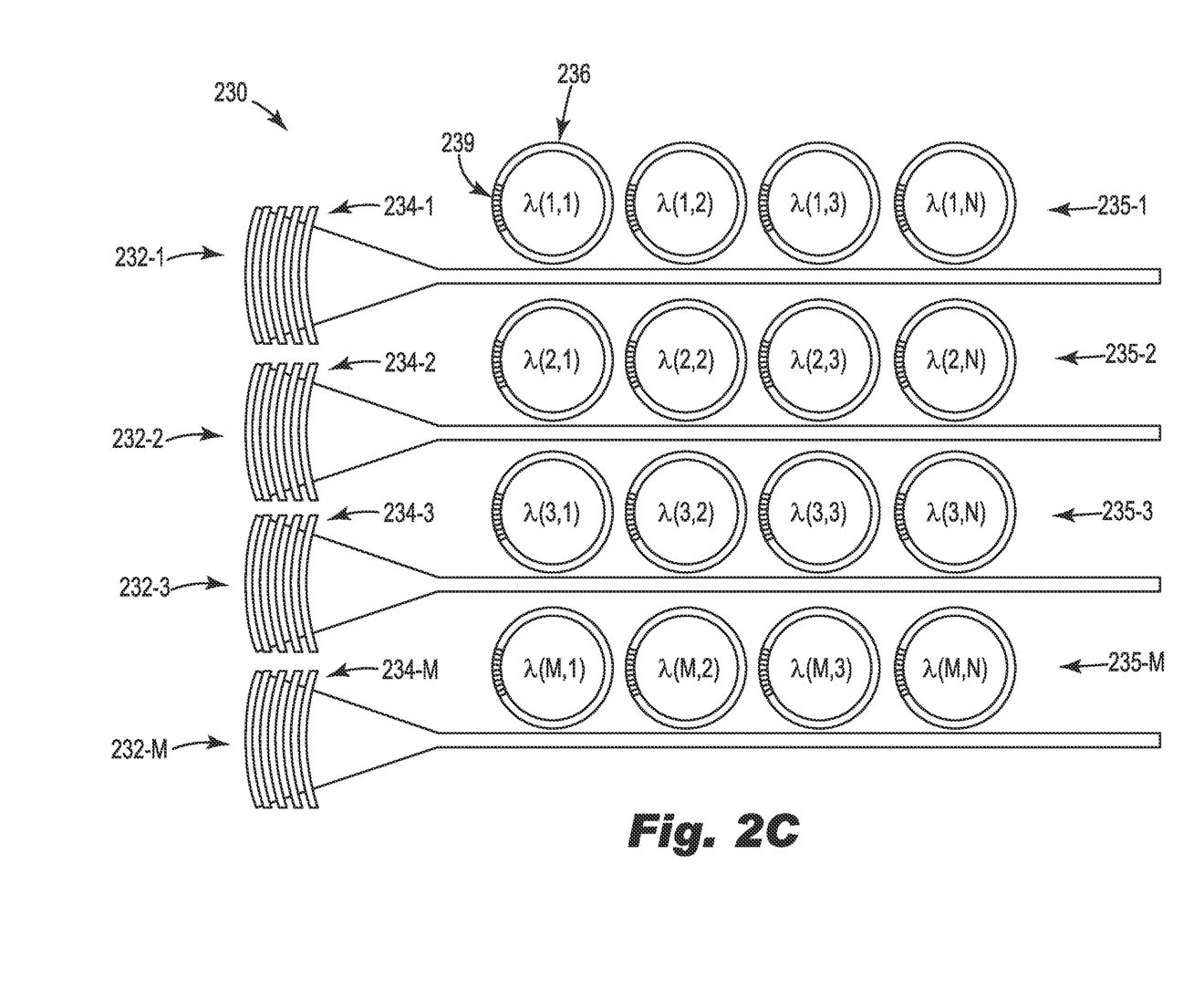

FIGS. 2A-2C illustrate examples of an array of input waveguides coupled to micro-ring optical resonators according to the present disclosure. As illustrated in FIGS. 2A-2C, the array of input waveguides 230 is shown from a top view perspective. The array of input waveguides 230 includes a plurality of input waveguides (e.g., input waveguides 232-1, 232-2, 232-3, and 232-M). By way of example, the plurality of input waveguides 230 shown in FIGS. 2A-2C is four, however, the present disclosure is not limited to four input waveguides in an array of input waveguides. That is, an array of input waveguides includes any number of input waveguides that is two or more such that the number of waveguides is unlimited (e.g., the number of waveguides can be more than a hundred in some examples).

In some examples, a number of the input waveguides 232-1, 232-2, 232-3, and 232-M can be integrated with an input coupler (e.g., positioned at or near an end of each waveguide). As illustrated in FIGS. 2A-2C, in some examples, a number of the input couplers can be grating couplers (e.g., grating couplers 234-1, 234-2, 234-3, and 242-M) positioned at (e.g., integrated with) the end of each input waveguide 232-1, 232-2, 232-3, and 232-M for collection (e.g., capture) of light to be analyzed. Such grating couplers 234-1, 234-2, 234-3, and 242-M can have a grating with a predetermined pitch, etch angle, and/or duty cycle for diffraction of incident light such that the incident light becomes light that travels in an intended direction along each of the input waveguides 232-1, 232-2, 232-3, and 232-M. As shown in FIGS. 2A-2C, the grating couplers 234-1, 234-2, 234-3, and 242-M are each illustrated as having a grating with gaps (e.g., corresponding to the predetermined pitch, etch angle, and/or duty cycle for diffraction of incident light). In various examples, the grating gaps can each be formed in a wall of a coupler/waveguide layer or the grating gaps can each be formed in a separate coupler material that is connected to the waveguide, among other configurations.

By way of example, the number of grating couplers shown in FIGS. 2A-2C is four, however, the present disclosure is not limited to four grating couplers in an array of input waveguides. That is, if the array of input waveguides has any grating couplers, the number of grating couplers can be any number from one to the number of input waveguides such that some input waveguides can have input couplers other than grating couplers, some input waveguides can share a grating coupler with a number of other input waveguides, or each input waveguide can be integrated with a grating coupler, among other examples. In some examples, an input waveguide can have a wider transition region to integrate with the grating coupler to provide a funnel for photons into a narrower pathway compared to an area of an incident light beam on the grating coupler.

Each of the plurality of input waveguides 232-1, 232-2, 232-3, and 232-M in the array 230 can, in various examples, have a plurality of micro-rings (e.g., 235-1, 235-2, 235-3, and 235-M) laterally offset therefrom. That is, for example, the plurality of micro-rings 235-1 can be offset from input waveguide 232-1, the plurality of micro-rings 235-2 can be offset from input waveguide 232-2, etc. By way of example, the plurality of micro-rings offset from each input waveguide shown in FIGS. 2A-2C is four, however, the present disclosure is not limited to four micro-rings offset from each input waveguide. That is, the plurality of micro-rings offset from each input waveguide includes any number of micro-rings that is two or more such that the number of micro-rings is unlimited (e.g., the number of micro-rings can be more than a hundred in some examples).

An example of a micro-ring optical resonator apparatus, as described herein, can include an array of input waveguides with each input waveguide optically coupled to an array of micro-rings. The micro-ring optical resonator apparatus can include an output waveguide operatively associated with each of the micro-rings and a scattering object operatively associated with each of the micro-rings, where the scattering object is connected to the output waveguide.

For example, as illustrated in FIG. 2A, the array of input waveguides 230 shows that a particular micro-ring 236, as described herein, can have an output waveguide 237 positioned within (e.g., inside) a circumference of the micro-ring 236. In some examples, the output waveguide 237 can be positioned substantially coplanar with the particular micro-ring 236. The output waveguide 237 can be configured to tap the light, energy and/or signals from the micro-ring 236. For example, a size and/or length of a gap between the output waveguide 237 and the micro-ring 236 can contribute to determining a rate (e.g., a coupling rate) at which the light, energy and/or signals are tapped from the micro-ring.

Coupling rates between input waveguides, output waveguides, and micro-rings, as described herein, can contribute to determining efficiency and/or resolution of the combination of the input waveguides, output waveguides, and the micro-rings. For example, a micro-ring can have an intrinsic loss due, in various examples, to combinations of material absorption, bending loss, and/or scattering loss (e.g., due to surface roughness). Efficiency can be increased, for example, by configuring the coupling rate of the input waveguide and/or output waveguide to be large relative to the intrinsic loss of the micro-ring, although increasing the efficiency as such may reduce frequency resolution (e.g., of a spectrometer). In contrast, frequency resolution can be increased, for example, by configuring the coupling rate of the input waveguide and/or output waveguide to be small relative to the intrinsic loss of the micro-ring, although increasing the frequency resolution as such may reduce the efficiency. In some examples, a compromise can be reached by configuring the coupling rate of the input waveguide and/or output waveguide to be comparable to the intrinsic loss of the micro-ring.

Factors in addition to the size and/or length of the gap between the output waveguide 237 and the micro-ring 236 can contribute to the coupling rate with the micro-ring (e.g., an arc diameter and/or curvature, length, and/or thickness of the output waveguide, and/or a particular material from which the output waveguide is formed, among other factors). In some examples, the coupling rate of a particular output waveguide can be determined experimentally and a number of these factors can be subsequently adjusted to achieve a desired coupling rate (e.g., at a particular frequency or range of frequencies of light, energy, and/or signals).

A scattering object 239 can, in various examples, be connected to (e.g., embedded into) each output waveguide 237. Each scattering object 239 can be formed with various configurations. For example, scattering objects can be formed as an output grating embedded into the output waveguide, a single facet at an end of the output waveguide that is etched substantially at a 45 degree angle from vertical, and/or as a metallic antenna affixed to the output waveguide, among other configurations. The scattering objects 239 can, for example, be designed to reduce backscattering of output. By way of example and not by way of limitation, backscattering of output can be reduced by an apodized output grating having facets etched substantially at a 45 degree angle from vertical.

A particular scattering object 239, as described herein, can be connected to (e.g., embedded into) an output waveguide 237 positioned within the circumference of the micro-ring 236. That is, a scattering object 239 also can be positioned within the circumference of the micro-ring 236. In some examples, a particular scattering object 239 can be positioned substantially coplanar with the particular micro-ring 236 and/or the particular output waveguide 237.

Each scattering object 239 can, in various examples, be configured to emit light, energy, and/or signals corresponding to a selected frequency or range of frequencies at which a particular micro-ring 236 resonates. For example, the frequency or frequencies at which each scattering object 239 connected to (e.g., embedded into) the output waveguide 237 will emit light, energy, and/or signals can depend on a number of factors related to the physical structure of each particular scattering object. Such factors can, for example, include an output grating having a predetermined pitch, etch angle, and/or duty cycle, among other factors. Backscattering of the emitted light, energy, and/or signals can be reduced, for example, by diffraction by the output grating such that the of light, energy, and/or signals travel in an intended direction away from the micro-ring 236, for example, toward the individual detectors 128 (e.g., photoactive sensors) of the measurement device 129 (e.g., a CCD) shown in FIG. 1.

As illustrated in FIG. 2B, another example of the array of input waveguides 230 shows that a particular micro-ring 236, as described herein, can have an output waveguide 237 positioned outside a circumference of the micro-ring 236. In some examples, the output waveguide 237 can be positioned substantially coplanar with the particular micro-ring 236. The output waveguide 237 can be configured to tap the light, energy and/or signals from the micro-ring 236. For example, a size and/or length of a gap between the output waveguide 237 and the micro-ring 236 can contribute to determining a rate (e.g., a coupling rate) at which the light, energy and/or signals are tapped from the micro-ring.

Factors in addition to the size and/or length of the gap between the output waveguide 237 and the micro-ring 236 can contribute to the coupling rate with the micro-ring (e.g., straightness, an arc diameter, and/or curvature, length, and/or thickness of the output waveguide, and/or a particular material from which the output waveguide is formed, among other factors). That is, the output waveguide 237 is shown to be straight in FIG. 2B by way of example and not by way of limitation. In some examples, the coupling rate of a particular output waveguide can be determined experimentally and a number of these factors can be subsequently adjusted to achieve a desired coupling rate (e.g., at a particular frequency or range of frequencies of light, energy, and/or signals).

A particular scattering object 239, as described herein, can be connected to (e.g., embedded into) the output waveguide 237 positioned outside the circumference of the micro-ring 236. That is, the scattering object 239 also can be positioned outside the circumference of the micro-ring 236. In some examples, the particular scattering object 239 can be positioned substantially coplanar with the particular micro-ring 236 and/or the particular output waveguide 237. A distance between the input waveguides and the output waveguides and the scattering objects is shown for convenience of illustration and not by way of limitation. That is, the distance between and/or a planarity of the input waveguides and the output waveguides and the scattering objects can be selected to enable proper operation thereof (e.g., to prevent inappropriate coupling, among other considerations).

Each scattering object 239 can, in various examples, be configured to emit light, energy, and/or signals corresponding to a selected frequency or range of frequencies at which a particular micro-ring 236 resonates. For example, the frequency or frequencies at which each scattering object 239 connected to (e.g., embedded into) the output waveguide 237 will emit light, energy, and/or signals can depend on a number of factors related to the physical structure of each particular scattering object. Such factors can, for example, include an output grating having a predetermined pitch, etch angle, and/or duty cycle, among other factors.

As illustrated in FIG. 2C, another example of the array of input waveguides 230 shows that a particular micro-ring 236, as described herein, can operate as its own output waveguide. A particular scattering object 239, as described herein, can be connected to (e.g., embedded into) the micro-ring 236 (e.g., operating as the output waveguide, as described herein). By way of example and not by way of limitation, an output grating can be formed as grooves in the micro-ring (e.g., shallow enough to maintain a resonator quality factor by keeping scattering sufficiently weak) and/or small protrusions (e.g., formed from the same material as or a material different from that of the micro-ring operating as the output waveguide).

Each scattering object 239 can, in various examples, be configured to emit light, energy, and/or signals corresponding to a selected frequency or range of frequencies at which a particular micro-ring 236 resonates. For example, the frequency or frequencies at which each scattering object 239 connected to (e.g., embedded into) the micro-ring 236 (e.g., operating as the output waveguide) will emit light, energy, and/or signals can depend on a number of factors related to the physical structure of each particular scattering object. Such factors can, for example, include an output grating having a predetermined pitch, etch angle, and/or duty cycle, among other factors.

Accordingly, each combination of a micro-ring 236, an output waveguide 237, and/or a scattering object 239 can be configured to emit a particular selected frequency or range of frequencies of light, energy, and/or signals. As such, each of the plurality of combinations of a micro-ring, an output waveguide, and/or a scattering object can be configured to emit a different selected frequency or range of frequencies of light, energy, and/or signals. For example, each combination of a micro-ring 236, an output waveguide 237, and/or a scattering object 239 illustrated in FIGS. 2A-2C as offset from input waveguide 232-1 can be configured to emit a particular selected frequency or range of frequencies of light, energy, and/or signals that are different from (e.g., are substantially non-overlapping with) those selected frequencies or ranges of frequencies to which others of the plurality are configured to emit.

These selected frequencies or ranges of frequencies to which each of the plurality of combinations of a micro-ring, an output waveguide, and/or a scattering object illustrated in FIGS. 2A-2C are configured to emit are represented by the symbol $\lambda$ (i,j). The symbol $\lambda$ indicates the particular selected frequencies or ranges of frequencies (e.g., as measured in cycles per second or radians per second) to which each of the plurality of combinations of a micro-ring, an output waveguide, and/or a scattering object are configured to emit. The variable i indicates a particular input waveguide to which the particular combination is offset and the variable j indicates a particular position in a sequential order in which the particular combination is placed. For example, the symbol $\lambda$ (1,1) can indicate that such a combination is configured for a particular selected frequency or range of frequencies to emit, that the combination is offset from the first input waveguide (e.g., input waveguide 232-1), and that the combination is first in the plurality of such combinations (e.g., 235-1) offset from the first waveguide. The last of such combinations can be indicated by the symbol $\lambda$ (1,N). Further, the symbol $\lambda$ (M,1) can indicate that such a combination is configured for a particular selected frequency or range of frequencies to emit, that the combination is offset from the last input waveguide (e.g., input waveguide 232-M), and that the combination is first in the plurality of such combinations (e.g., 235-M) offset from the last waveguide. The last of such combinations can be indicated by the symbol $\lambda$ (M,N). The combinations of a micro-ring, an output waveguide, and/or a scattering object, as illustrated in FIGS. 2A-2C, offset from input waveguides between the first and last input waveguides can be indicated accordingly and sequentially with similar symbols.

Hence, the array of input waveguides 230 as illustrated in FIGS. 2A-2C, can be configured to analyze, for example, a large range of frequencies in an input light sample. The large range of frequencies can be analyzed because each combination of a micro-ring, an output waveguide, and/or a scattering object can be configured to emit a particular selected frequency or range of frequencies of light, energy, and/or signals that are different from those selected frequencies or ranges of frequencies to which others are configured to emit.

Moreover, each combination of a micro-ring, an output waveguide, and/or a scattering object at each particular position offset from each of the input waveguides can be configured to emit substantially the same selected frequency or range of frequencies. For example, the $\lambda$ (1,1), $\lambda$ (2,1), $\lambda$ (3,1), and $\lambda$ (M,1) combinations of micro-rings, output waveguides, and/or a scattering object can all be configured to emit substantially the same selected frequency or range of frequencies, the $\lambda$ (1,2), $\lambda$ (2,2), $\lambda$ (3,2), and $\lambda$ (M,2) combinations of micro-rings, output waveguides, and/or a scattering object can all be configured emit substantially the same selected frequency or range of frequencies, etc. That is, each combination of a micro-ring, an output waveguide, and/or a scattering object at each particular position in the plurality offset from each of the input waveguides (e.g., 232-1, 232-2, 232-3, 232-M) can be configured to emit substantially the same selected frequency or range of frequencies (e.g., configured redundantly).

An array of input waveguides 230 (e.g., with grating couplers 234-1, 234-2, 234-3, and 242-M positioned adjacently across a width) that has each combination of micro-ring, output waveguide, and/or a scattering object at each particular position in the plurality offset from each of the input waveguides (e.g., 232-1, 232-2, 232-3, 232-M) can, for example, provide redundancy in output of frequencies or ranges of frequencies of light, energy, and/or signals. Such redundancy can be used to compensate for random variation in, for example, micro-ring resonance frequencies (e.g., by calibration, post-processing, etc.) in analysis and/or construction of a spectrum for the input light.

The array of input waveguides 230 with an array of light inputs (e.g., grating couplers 234-1, 234-2, 234-3, and 242-M) positioned adjacently across a width (e.g., orthogonal to a direction of input light) can functionally have a broader "entrance slit" than a conventional spectrometer. As such, an increased "throughput" of input light can be enabled. The increased throughput of input light can be useful when the light originates from a spatially extended source. A spatially extended source can, for example, be a source of light with a diameter larger than a diffraction-limited spatial resolution of the collection optics, which can be approximated by the wavelength of light divided by twice the numerical value of the collection optics.

In some examples, input light can be focused into the input couplers (e.g., grating couplers) to provide a collimated input of different light bands (e.g., via a prism and/or a grating, among other means). A bandwidth focused into each of the input couplers can be smaller that a free spectral range (FSR) provided by the light, energy, and/or signals emitted from the combinations of the micro-ring, output waveguide, and/or output grating in order to provide acceptable resolution over the bandwidth.

Figure 3:
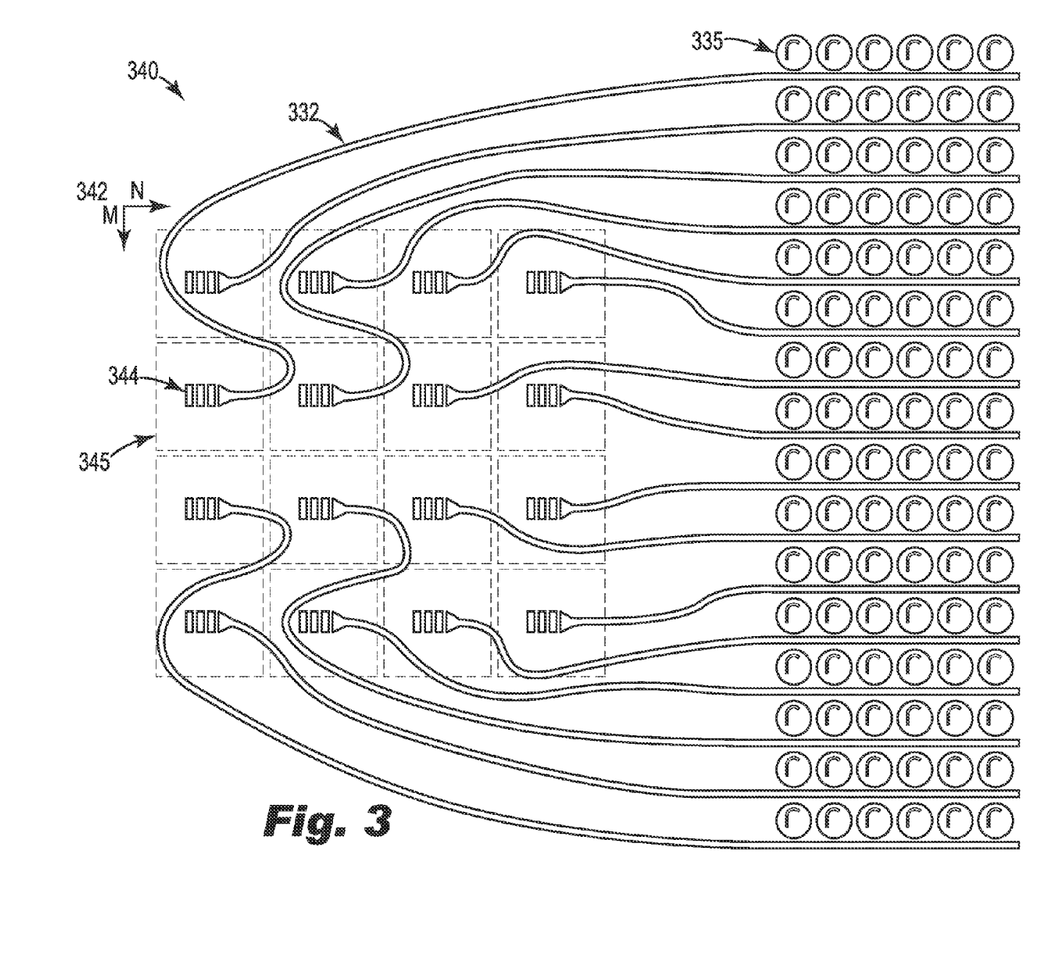
FIG. 3 is another example of an array of input waveguides coupled to micro-ring optical resonators according to the present disclosure.

FIG. 3 is another example of an array of input waveguides coupled to micro-ring optical resonators according to the present disclosure. As illustrated in FIG. 3, the array of input waveguides 340 is shown from a top view perspective. The array of input waveguides 340 includes a plurality of input waveguides (e.g., input waveguide 332). By way of example, the plurality of input waveguides in the array 340 shown in FIG. 2 is sixteen, however, the present disclosure is not limited to sixteen input waveguides in an array of input waveguides. That is, an array of input waveguides includes any number of input waveguides that is two or more such that the number of input waveguides is unlimited (e.g., the number of input waveguides can be more than a hundred in some examples).

In some examples, a number of the input waveguides 332 can be coupled to (e.g., integrated with) an input coupler (e.g., positioned at or near an end of each waveguide). As illustrated in FIG. 3, in some examples, a number of the input couplers can be grating couplers (e.g., grating coupler 344) positioned at or near (e.g., integrated with) the end of each input waveguide 332 for collection (e.g., capture) of light to be analyzed. Such grating couplers 344 can have a grating with a predetermined pitch, etch angle, and/or duty cycle for diffraction of incident light such that the incident light becomes light that travels in an intended direction along each of the input waveguides 332.

By way of example, the number of grating couplers shown in FIG. 3 is sixteen, however, the present disclosure is not limited to sixteen grating couplers in an array of input waveguides. That is, if the array of input waveguides has any grating couplers, the number of grating couplers can be any number from one to the number of input waveguides such that some input waveguides can have input couplers other than grating couplers, some input waveguides can share a grating coupler with a number of other input waveguides, or each input waveguide can be integrated with a grating coupler, among other examples. In some examples, an input waveguide can have a wider transition region to integrate with the grating coupler to provide a funnel for photons into a narrower pathway compared to an area of an incident light beam on the grating coupler.

The plurality of input couplers (e.g., grating coupler 344) can be positioned in a two-dimensional grid 342 such that, for example, each of the input couplers (e.g., grating coupler 344) is separated by at least a particular distance from other input couplers. By way of example and not by way of limitation, FIG. 3 shows each of the plurality of grating couplers (e.g., 344) positioned substantially in a center of a square (e.g., 345). A plurality of grating couplers can be positioned in a vertical M direction and a plurality grating couplers can be positioned in a horizontal N direction to form the two-dimensional grid 342. The number of grating couplers in the M direction can be two or more, as can the number of grating couplers in the N direction, and the number of grating couplers in the M and N directions can be different such that the number of grating couplers is unlimited (e.g., the number of grating couplers can be more than a hundred in some examples). In some examples, at least one of the squares (e.g., 345) can represent a micro-lens to concentrate light into a grating coupler positioned below the micro-lens In various examples, each of the plurality of grating couplers (e.g., 344) can be positioned at or near (e.g., integrated with) the end of each input waveguide (e.g., 332) for collection (e.g., capture) of light to be analyzed. As shown in FIG. 3, the grating couplers can be spaced (e.g., positioned such that the grating couplers are substantially in a center of a larger square and/or below a micro-lens) to enable the input waveguides (e.g., 332) to be routed around the grating couplers.

In various examples, each of the grating couplers (e.g., 344) can be configured to collect and/or redirect substantially the same range of frequencies of input light. In various examples, each of the input waveguides (e.g., 332) can be configured to retain and/or transmit substantially the same range of frequencies of light, which can be substantially the same as the range of frequencies collected and/or redirected by the grating couplers. As such, in some examples, the plurality of grating couplers each integrated with one of a plurality of input waveguides can enable the two-dimensional grid 342 to have a high degree of redundancy for collection and/or transmission of a particular range of input light.

As shown in and described in further detail with regard to FIGS. 2A-2C, each of the plurality of input waveguides (e.g., 332) in the array 340 shown in FIG. 3 can, in various examples, have a plurality (e.g., an array) of micro-rings (e.g., 335) laterally offset therefrom. By way of example, the plurality of micro-rings offset from each input waveguide shown in FIG. 3 is six, however, the present disclosure is not limited to six micro-rings offset from each waveguide. That is, the plurality of micro-rings offset from each input waveguide includes any number of micro-rings that is two or more such that the number of micro-rings is unlimited (e.g., the number of micro-rings can be more than a hundred in some examples). Moreover, the positioning of the output waveguides and scattering objects within (e.g., inside) the circumference of the micro-rings is by way of example and not by way of limitation.

Each combination, as described herein, of a micro-ring, an output waveguide, and/or, for example, an output grating can be configured emit a particular selected frequency or range of frequencies of light, energy, and/or signals, which can be different from (e.g., are substantially non-overlapping with) other such combinations in, for example, a sequential and/or linear plurality (e.g., at 335). In some examples, each combination of a micro-ring, an output waveguide, and/or an output grating at each particular position (e.g., in the sequential and/or linear plurality) offset from each of the input waveguides can be configured to emit substantially the same selected frequency or range of frequencies (e.g., configured redundantly).

The array of input waveguides 340 can have grating couplers 344 positioned over a two-dimensional grid 342 that each collect and/or redirect substantially the same range of frequencies of input light into each of a plurality of input waveguides 332 that are configured to retain and/or transmit substantially the same range of frequencies of light. In some examples, a substantially complete spectrum of input light can be collected and/or redirected by each grating coupler. Moreover, each sequence of combinations of micro-ring, output waveguide, and/or output grating can be configured such that each such combination at each particular position in the plurality offset from each of the input waveguides emits substantially the same selected frequency or range of frequencies. Accordingly, such a combination of grating couplers, input waveguides, micro-rings, output waveguides, and/or output gratings can provide redundancy in output of frequencies or ranges of frequencies of light, energy, and/or signals.

Such redundancy can be used to compensate for random variation in, for example, micro-ring resonance frequencies (e.g., by calibration, post-processing, etc.) in analysis and/or construction of a spectrum for the input light and/or provide an increased "throughput" of input light when the light originates from a spatially extended source (e.g., a source of light with a diameter larger than a wavelength of light). More input light can, in some examples, be collected (e.g., captured) by positioning a micro-lens over at least some of the grating couplers and/or tiles of the array 340.

As just described, a "hyperspectral imager" can be constructed. A two-dimensional array can, for example, have 100 input couplers (e.g., grating couplers) in the M direction and 100 input couplers (e.g., grating couplers) in the N direction. Each of the resultant 10,000 input couplers in the two-dimensional grid can collect and/or redirect substantially the same range of frequencies of input light into each of a plurality of input waveguides (e.g., 10,000 input waveguides) that are configured to retain and/or transmit substantially the same range of frequencies of light.

Moreover, each input waveguide can, for example, have an offset linear sequence of combinations of micro-ring, output waveguide, and/or output grating configured such that each such combination at each particular position in the plurality offset from each of the input waveguides emits substantially the same selected frequency or range of frequencies. There can, for example, be 1,000 different combinations of micro-ring, output waveguide, and/or output grating in each linear sequence that emit 1,000 different selected frequencies or ranges of frequencies of light, energy, and/or signals (e.g., which are substantially non-overlapping). Accordingly, the light of the 10,000 input coupler/waveguide inputs can each be sensed by 1,000 of substantially the same linear sequences of combinations of micro-ring, output waveguide, and/or output grating.

When each of the 1,000 different selected frequencies or ranges of frequencies and/or emissions of light, energy, and/or signals are substantially non-overlapping, substantially 1,000 channels of spectral resolution can be provided for each of the 10,000 input coupler/waveguide inputs. Each of the 10,000,000 outputs of light, energy, and/or signals can be sensed, for example, with individual detectors (e.g., photoactive sensors) of a measurement device (e.g., a CCD) as shown in FIG. 1.

Such an arrangement can operate as a hyperspectral imager of a broad band of frequencies through a band range of frequencies. The breadth of the frequency band can be determined, for example, by whether the input couplers (e.g., grating couplers) are configured to collect (e.g., capture) a broad or a narrow band of frequencies, whether the input waveguides are configured to retain and/or transmit a broad or a narrow band of frequencies, and/or whether the combinations of micro-rings, output waveguides, and/or output gratings are configured emit a broad or a narrow band of frequencies, among other considerations.

A quality factor (i.e., Q) is a dimensionless parameter that describes how under-damped an oscillator or a resonator is, which can reflect a resonator's bandwidth relative to its center frequency. A higher Q can indicate a lower rate of energy loss relative to a stored energy (e.g., a resonance frequency dampens more slowly). A range of frequencies at which a resonator resonates is the bandwidth and resonators with a higher Q operate over a smaller range of frequencies and are more stable. The Q can vary substantially between systems. Systems for which damping is important have a low Q (e.g., a door having a damper to prevent it from slamming shut can have a Q of about 0.5). In contrast, other systems in which strong resonance and/or high frequency stability are desired have a substantially higher Q (e.g., tuning forks can have a Q of around 1,000 and atomic clocks can have a Q of $10^{11}$ or more).

Systems as just described, for example, have been experimentally determined to have approximately 20 gigahertz (GHz) resolution at approximately 630 nanometers (nm) of input light wavelength with a relatively high Q of 20,000. For instance, given an example of a 10 micrometer (μm) micro-ring having a free spectral range (FSR) of 5,000 GHz, approximately 1,000 such micro-rings selected to resonate to substantially non-overlapping frequency ranges would provide complete visible spectrum coverage.

Hence, an example of a micro-ring optical resonator apparatus, as described herein, can include an input waveguide (e.g., 232, 332) optically coupled to an array of micro-rings (e.g., 235, 335), where each of the micro-rings resonates at a selected optical frequency or range of frequencies that is a subset of optical frequencies resonated by the array of micro-rings. For example, the array of micro-rings (e.g., 235, 335) can be a longitudinal series (e.g., sequentially linear) of micro-rings that is laterally offset from each input waveguide (e.g., 232, 332).

The apparatus can include a measurement device (e.g., 129), in various examples, to collect energy emitted by the output gratings (e.g., 239). In some examples, the measurement device (e.g., 129) can include a CCD with photoactive sensors (e.g., 128), where at least one photoactive sensor is co-aligned with the output grating of at least one of the micro-rings.

In some examples, an input grating coupler (e.g., 234, 334) can be connected to (e.g., integrated with) the input waveguide (e.g., 232, 332) to collect the optical frequencies resonated by the array of micro-rings (e.g., 235, 335). The array of input waveguides can, in various examples, be a two-dimensional array (e.g., 230, 340), where at least one of a plurality of longitudinal series of micro-rings (e.g., 235, 335) is laterally offset from one of a plurality of laterally offset input waveguides (e.g., 232-1, 232-2, 232-3, and 232-M). The input grating coupler of each of the laterally offset input waveguides can, in some examples, collect substantially the same optical frequencies. Each of the micro-rings can be at a defined position in each of the plurality of longitudinal series of micro-rings and each of the micro-rings at that defined position can resonate at substantially the same selected optical frequency or range of frequencies (e.g., λ (1,1), λ (2,1), λ (3,1), and λ (M,1) in FIG. 2).

Figure 4:
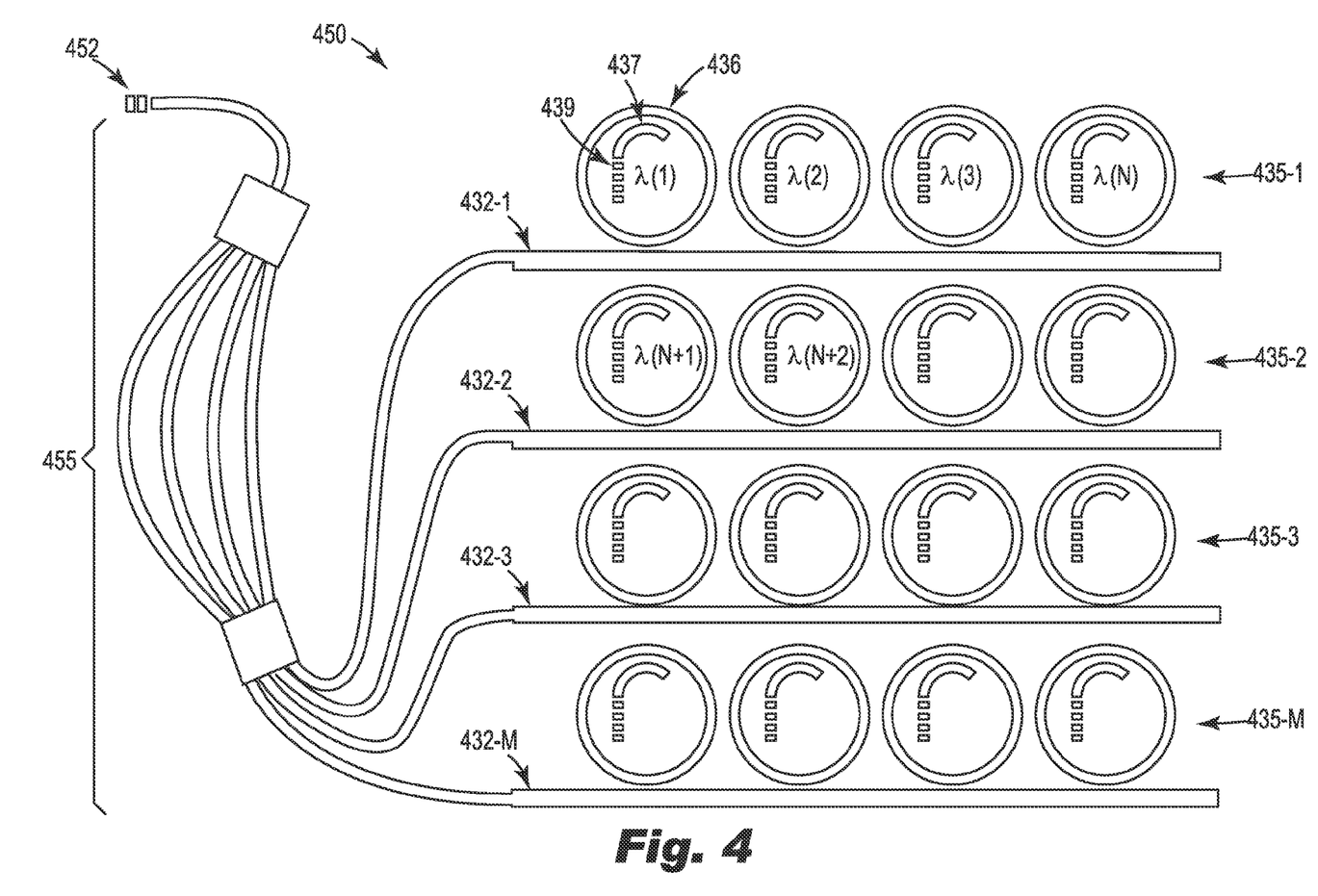
FIG. 4 illustrates an example of a coarse frequency sorting element for input of light into an array of input waveguides coupled to micro-ring optical resonators according to the present disclosure.

FIG. 4 illustrates an example of a coarse frequency sorting element for input of light into an array of input waveguides coupled to micro-ring optical resonators according to the present disclosure. As illustrated in FIG. 4, the array of input waveguides 450 is shown from a top view perspective. The array of input waveguides 450 includes a plurality of input waveguides (e.g., input waveguides 432-1, 432-2, 432-2, and 432-M). By way of example, the plurality of input waveguides shown in FIG. 4 is four, however, the present disclosure is not limited to four input waveguides in an array of input waveguides. That is, an array of input waveguides includes any number of input waveguides that is two or more such that the number of input waveguides is unlimited (e.g., the number of input waveguides can be more than a hundred in some examples). Moreover, the positioning of the output waveguides and scattering objects within (e.g., inside) the circumference of the micro-rings is by way of example and not by way of limitation.

In some examples, the plurality of input waveguides (e.g., 432-1, 432-2, 432-2, and 432-M) can each be connected to (e.g., integrated with) a coarse frequency sorting element 455 (e.g., positioned at or near an end of each waveguide). The coarse frequency sorting element 455 can be connected to (e.g., integrated with) a broadband input coupler 452. The broadband input coupler 452 can, for example, be positioned at or near an end of the coarse frequency sorting element 455 that is distal to the plurality of input waveguides (e.g., 432-1, 432-2, 432-2, and 432-M). The broadband input coupler 452 illustrated in FIG. 4 can, for example, occupy less area and/or space than the pluralities of input couplers (e.g., grating couplers) shown in FIGS. 2 and 3. Whereas some configurations of grating couplers can be utilized as the coarse frequency sorting element 455, other possibilities include a polished end facet, a single 45-degree facet obtained by dry or wet etching processes or by focused ion beam milling, and/or by inclusion of a metallic scatterer, among others.

In some examples, an arrayed wavelength grating (AWG), as illustrated in FIG. 4, can be utilized as the coarse frequency sorting element 455. For an AWG, incoming light (e.g., provided by the broadband input coupler 452) can traverse a first free space propagation region and enter a bundle of separate channel waveguides. The channel waveguides have different lengths and thus apply a different phase shift at the exit of the channel waveguides as the light traverses into a second free space propagation region where each of the discrete wavelengths can be output into separate input waveguides (e.g., 432-1, 432-2, 432-2, and 432-M). When operated as just described, the AWG functions as a demultiplexer. As such, the AWG can be used to create separate bands (e.g., individual channels) of different frequencies for input into the separate input waveguides (e.g., 432-1, 432-2, 432-2, and 432-M).

In some examples, an on-chip grating (e.g., an echelle grating) can be utilized as the coarse frequency sorting element 455 to create separate bands (e.g., individual channels) of different frequencies for input into the separate input waveguides. For instance, the on-chip grating can occupy less area and/or space than the AWG.

As described in further detail with regard to FIGS. 2A-2C, each of the plurality of input waveguides 432-1, 432-2, 432-2, and 432-M in the array 450 shown in FIG. 4 can, in various examples, have a plurality of micro-rings (e.g., 435-1, 435-2, 435-3, and 435-M) laterally offset therefrom. A particular micro-ring 436, as described herein, can have an output waveguide 437 positioned within a circumference of the micro-ring 436. A scattering object 439 can, in various examples, be connected to each output waveguide 437. Each combination of a micro-ring 436, an output waveguide 437, and, for example, an output grating 439 can be configured to emit a particular selected frequency or range of frequencies of light, energy, and/or signals. As such, each of the plurality of combinations of a micro-ring, an output waveguide, and, for example, an output grating can be configured to, for example, emit a different selected frequency or range of frequencies of light, energy, and/or signals.

For example, each combination of a micro-ring 436, an output waveguide 437, and an output grating 439 illustrated in FIG. 4 as offset from input waveguide 432-1 can be configured to emit a particular selected frequency or range of frequencies of light, energy, and/or signals that are different from (e.g., are substantially non-overlapping with) those selected frequencies or ranges of frequencies to which others of the plurality are configured to emit.

These selected frequencies or ranges of frequencies to which each of the plurality of combinations of a micro-ring, an output waveguide, and an output grating illustrated in FIG. 4 are configured to emit are represented by the symbol λ (x), where λ indicates the particular selected frequencies or ranges of frequencies (e.g., as measured in cycles per second or radians per second) to which each of the plurality of combinations of a micro-ring, an output waveguide, and an output grating are configured to emit. For example, the symbol λ (1) can indicate that such a combination is configured for a particular selected frequency or range of frequencies to emit, and that the combination is first in the plurality of such combinations (e.g., 435-1) offset from the first input waveguide (e.g., 432-1). The last of such combinations offset from the first input waveguide (e.g., 432-1) can be indicated by the symbol λ (N).

The band of frequencies input into the second input waveguide (e.g., 432-2) is different from the band of frequencies input into the first input waveguide (e.g., 432-1). As such, the plurality of combinations (e.g., 435-2) offset from the second input waveguide (e.g., 432-2) is configured for a particular range of frequencies emit that is different from (e.g., substantially non-overlapping with) the plurality of combinations (e.g., 435-1) offset from the first input waveguide (e.g., 432-1). Accordingly, the symbol λ (N+1) can indicate the first of such combinations configured for a particular selected frequency or range of frequencies to emit that is offset from the second input waveguide (e.g., input waveguide 432-2), where N 1 indicates a sequential difference from N offset from the first input waveguide (e.g., 432-1). The symbol λ (N+2) can indicate the second of such combinations configured for a different particular selected frequency or range of frequencies emit that is offset from the second waveguide. The combinations of a micro-ring, an output waveguide, and an output grating, as illustrated in FIG. 4, offset from input waveguides between the first and last input waveguides can be indicated accordingly and sequentially with similar symbols.

As such, an array 450 of input waveguides as illustrated in FIG. 4, can be configured to analyze, for example, a large range of frequencies in an input light sample. The large range of frequencies can be analyzed because each combination of a micro-ring, an output waveguide, and an output grating can be configured emit a particular selected frequency or range of frequencies of light, energy, and/or signals that are different from those selected frequencies or ranges of frequencies to which others are configured to emit.

Hence, an example of the present disclosure includes a micro-ring optical resonator system including a plurality (e.g., an array) of input waveguides (e.g., 432-1, 432-2, 432-2, and 432-M) with each input waveguide optically coupled to a longitudinal series of micro-rings (e.g., 435-1, 435-2, 435-3, and 435-M). An output waveguide (e.g., 437) can, in various examples, be operatively associated with (e.g., positioned within or outside a circumference of at least one of the micro-rings to couple therewith or the micro-ring can operate as the output waveguide) and a scattering object (e.g., 439) operatively associated with, in various examples, at least one of the micro-rings, where the scattering object is connected to the output waveguide.

The system can include a measurement device (e.g., 129), in various examples, to collect energy emitted by the output gratings (e.g., 239). In some examples, the measurement device (e.g., 129) can include a CCD with photoactive sensors (e.g., 128), where at least one photoactive sensor is co-aligned with the output grating of at least one of the micro-rings.

In some examples the system can include a coarse frequency sorting element (e.g., 455) for separation of input light into a plurality of different output ranges of optical frequencies, where the plurality of different output ranges of optical frequencies is input to the array of input waveguides. In various examples, each of the micro-rings (e.g., in a sequential plurality of micro-rings, such as 435-1, 435-2, 435-3, and 435-M) can resonate at a selected optical frequency or range of frequencies that is a subset of the plurality of different input ranges of optical frequencies output by the coarse frequency sorting element (e.g., 455). A broadband input coupler (e.g., 452), in various examples as described herein, can be used to collect the light for the coarse frequency sorting element (e.g., 455).

Figure 5:
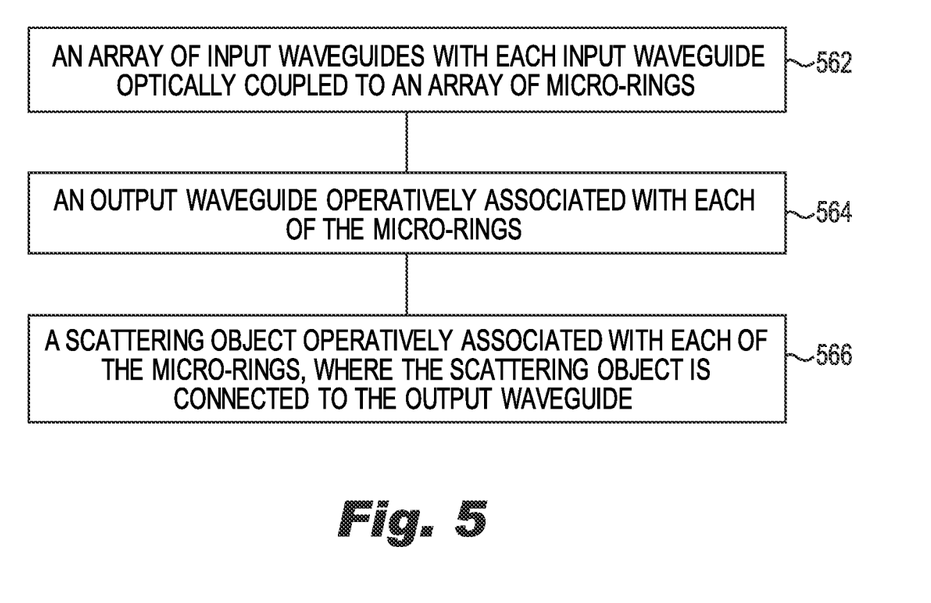
FIG. 5 is block diagram illustrating an example of a micro-ring optical resonator apparatus according to the present disclosure.

FIG. 5 is block diagram illustrating an example of a micro-ring optical resonator apparatus according to the present disclosure. As described in detail herein, an example of a micro-ring optical resonator apparatus can include an array of input waveguides with each input waveguide optically coupled to an array of micro-rings, as shown in block 562 of FIG. 5. An output waveguide can be operatively associated with each of the micro-rings, as shown in block 564. Further, a scattering object can be operatively associated with each of the micro-rings, where the scattering object is connected to the output waveguide, as shown in block 566.

As such, a method of utilizing a micro-ring optical resonator can include optically coupling each input waveguide of an array of input waveguides to an array of micro-rings, operatively coupling each of the micro-rings with an output waveguide, and connecting the output waveguide to a scattering object operatively associated with each of the micro-rings. Unless explicitly stated, the method examples described herein are not constrained to a particular order or sequence. Additionally, some of the described method examples, or elements thereof, can occur or be performed at the same, or substantially the same, point in time.

In various examples, an input waveguide (e.g., 114 in FIG. 1, 232 in FIG. 2, 332 in FIGS. 3, and 432 in FIG. 4) can be optically coupled with the micro-ring. Such optical coupling can depend on a number of factors including positioning the input waveguide an appropriate distance (e.g., laterally offset) from the micro-ring, and having a frequency or range of frequencies of light being transmitted by the input waveguide with which the micro-ring is capable of resonating (e.g., dependent on a diameter, circumference, and/or thickness of the micro-ring, a proportion of the diameter contributing to a hole in the middle of the micro-ring, and/or a particular material or compound from which the micro-ring is formed), among other factors. Optically coupling the input waveguide can include transferring optical energy at the selected optical frequency or range of frequencies from the input waveguide to the micro-ring.

The output waveguide also can, in various examples, be optically (e.g., evanescently) coupled with the micro-ring. Such optical coupling can depend on a number of factors including positioning the output waveguide an appropriate distance from the micro-ring, an arc diameter, straightness, and/or curvature, length, and/or thickness of the output waveguide, and/or a particular material from which the output waveguide is formed, among other factors. Energy (e.g., light and/or other electromagnetic signals) can, in various examples, be emitted from the scattering object, the energy corresponding to the selected optical frequency or range of frequencies to which the micro-ring resonates.

The apparatuses, systems, and methods for micro-ring optical resonators described herein can be implemented as a chip-based device (e.g., using semiconductor micro-technology) that uses two-dimensional layouts of micro-ring resonators coupled to input waveguides (e.g., for an on-chip spectrometer, among other applications). For example, such a chip-based device can function as a sophisticated optical filter that can be coupled to a measurement device, such as a CCD chip. Such a combination can take a large number of parallel inputs and generate a spectrographic pattern from which a spectrum can be computed for each input, while making efficient use of the space on a chip. The spectrographic pattern can provide 20 GHz or better resolution for substantially 1,000 input channels per input waveguide, thereby providing substantially 1,000 channels of spectral resolution. The light inputs can be arranged either in a linear configuration orthogonal to the incoming direction of the input light (e.g., as an alternative to an entrance slit of a conventional spectrometer) or in an array (e.g., for hyperspectral imaging).

Examples of the present disclosure can include micro-ring optical resonator apparatuses, systems, and methods, including executable instructions and/or logic to facilitate fabricating and/or operating the micro-ring optical resonator apparatuses. Processing resources can include one or more processors able to access data stored in memory to execute the formations, actions, functions, etc., as described herein. As used herein, "logic" is an alternative or additional processing resource to execute the formations, actions, functions, etc., described herein, which includes hardware (e.g., various forms of transistor logic, application specific integrated circuits (ASICs), etc.), as opposed to computer executable instructions (e.g., software, firmware, etc.) stored in memory and executable by a processor.

It is to be understood that the descriptions presented herein have been made in an illustrative manner and not a restrictive manner. Although specific examples for apparatuses, systems, methods, computing devices, and instructions have been illustrated and described herein, other equivalent component arrangements, instructions, and/or device logic can be substituted for the specific examples presented herein without departing from the spirit and scope of the present disclosure.

What is claimed:
1. A micro-ring optical resonator apparatus, comprising:
   an array of input waveguides with each input waveguide optically coupled to an array of micro-rings;
   an output waveguide operatively associated with each of the micro-rings;

a scattering object operatively associated with each of the micro-rings, wherein the scattering object is physically connected to the output waveguide; and a measurement device formed on a chip to collect energy emitted by the scattering objects, wherein at least one photoactive sensor on the chip is physically unconnected to and co-aligned with the scattering object of at least one of the micro-rings.

2. The apparatus of claim 1, wherein the output waveguide and the scattering object are within a circumference of each of the micro-rings.

3. The apparatus of claim 1, wherein the output waveguide and the scattering object are outside a circumference of each of the micro-rings.

4. The apparatus of claim 1, wherein each of the micro-rings operates as the output waveguide and the scattering object is connected to each of the micro-rings.

5. The apparatus of claim 1, wherein each of the micro-rings resonates at a selected optical frequency or range of frequencies that is a subset of optical frequencies resonated by the array of micro-rings.

6. The apparatus e of claim 1, wherein the array of micro-rings is a longitudinal series of micro-rings laterally offset from each input waveguide.

7. The apparatus of claim 1, wherein the array of input waveguides is a two-dimensional array, wherein at least one of a plurality of longitudinal series of micro-rings is laterally offset from one of a plurality of laterally offset input waveguides.

8. A micro-ring optical resonator system, comprising:
an array of input waveguides with each input waveguide optically coupled to a longitudinal series of micro-rings;
an output waveguide operatively associated with each of the micro-rings;
an output grating operatively associated with each of the micro-rings, wherein the output grating is physically connected to the output waveguide; and
a measurement device formed on a chip to collect energy emitted by the output gratings, wherein at least one photoactive sensor on the chip is is physically unconnected to and co-aligned with the output grating of at least one of the micro-rings.

9. The system of claim 8, wherein the measurement device comprises a charge coupled device with photoactive sensors on the chip.

10. The system of claim 8, comprising a coarse frequency sorting element for separation of input light into a plurality of different output ranges of optical frequencies, wherein the plurality of different output ranges of optical frequencies is input to the array of input waveguides.

11. The system of claim 10, comprising a broadband input coupler to collect the light for the coarse frequency sorting element.

12. The system of claim 8, comprising an input grating coupler connected to the input waveguide to collect optical frequencies resonated by the longitudinal series of micro-rings.

13. The system of claim 12, wherein the input grating coupler of each of a laterally offset array of input waveguides collects substantially the same optical frequencies.

14. The system of claim 13, wherein each of the micro-rings at a defined position in each of a plurality of longitudinal series of micro-rings resonates at a selected optical frequency or range of frequencies.

15. The system of claim 8, wherein the output waveguide is substantially coplanar with each of the micro-rings.

16. The system of claim 8, wherein the output grating is substantially coplanar with each of the micro-rings.

17. A method of utilizing a micro-ring optical resonator, comprising:
optically coupling each input waveguide of an array of input waveguides to an array of micro-rings;
operatively coupling each of the micro-rings with an output waveguide;
physically connecting the output waveguide to a scattering object operatively associated with each of the micro-rings; and
forming a measurement device on a chip to collect energy emitted by the scattering objects, wherein a plurality of photoactive sensors on the chip are each physically unconnected to and co-aligned with the scattering objects of a plurality of micro-rings.

18. The method of claim 17, further comprising evanescently coupling the output waveguide with a micro-ring.

19. The method of claim 17, wherein optically coupling the input waveguide comprises transferring optical energy at a selected optical frequency or range of frequencies from the input waveguide to a micro-ring.

20. The method of claim 19, further comprising emitting energy from the scattering object corresponding to the selected optical frequency or range of frequencies.

* * * * *

UNITED STATES PATENT AND TRADEMARK OFFICE
CERTIFICATE OF CORRECTION

| | | Page 1 of 1 |
|---|---|---|
| PATENT NO. | : 9,170,371 B2 | |
| APPLICATION NO. | : 13/454462 | |
| DATED | : October 27, 2015 | |
| INVENTOR(S) | : Charles M. Santori et al. | |

It is certified that error appears in the above-identified patent and that said Letters Patent is hereby corrected as shown below:

In the Claims

In column 17, line 22, in Claim 6, delete "apparatus e of" and insert -- apparatus of --, therefor.

In column 17, line 40, in Claim 8, delete "is is" and insert -- is --, therefor.

Signed and Sealed this
Twenty-second Day of March, 2016

Michelle K. Lee
*Director of the United States Patent and Trademark Office*